(12) United States Patent
Zarkadas et al.

(10) Patent No.: US 9,239,305 B2
(45) Date of Patent: Jan. 19, 2016

(54) SAMPLE HOLDER

(71) Applicant: PANalytical B.V., Almelo (NL)

(72) Inventors: Charalampos Zarkadas, Almelo (NL); Ian Torquels Campbell, Almelo (NL); Youhong Xiao, Almelo (NL)

(73) Assignee: PANALYTICAL B.V., Almelo (NL)

( * ) Notice: Subject to any disclaimer, the term of this patent is extended or adjusted under 35 U.S.C. 154(b) by 275 days.

(21) Appl. No.: 13/869,693

(22) Filed: Apr. 24, 2013

(65) Prior Publication Data

US 2014/0146940 A1    May 29, 2014

(30) Foreign Application Priority Data

Apr. 26, 2012  (EP) .................................... 12165715

(51) Int. Cl.
  *G01N 23/223* (2006.01)
  *G01N 23/22* (2006.01)
  *B01L 3/00* (2006.01)

(52) U.S. Cl.
  CPC .............. *G01N 23/223* (2013.01); *B01L 3/508* (2013.01); *G01N 23/22* (2013.01); *G01N 23/2204* (2013.01); *B01L 2200/025* (2013.01); *B01L 2300/0654* (2013.01); *B01L 2300/0803* (2013.01)

(58) Field of Classification Search
  CPC .. G01N 23/22; G01N 23/2204; G01N 23/223
  USPC .............................................. 378/44–50, 208
  See application file for complete search history.

(56) References Cited

U.S. PATENT DOCUMENTS

| | | | | |
|---|---|---|---|---|
| 3,378,684 A | * | 4/1968 | Mentink et al. | 250/428 |
| 4,037,109 A | | 7/1977 | Hosokwa et al. | |
| 4,346,299 A | * | 8/1982 | Mitteldorf et al. | 378/204 |
| 4,448,311 A | * | 5/1984 | Houser | 206/527 |
| 4,575,869 A | * | 3/1986 | Torrisi et al. | 378/47 |
| 4,587,666 A | * | 5/1986 | Torrisi et al. | 378/47 |
| 4,643,033 A | * | 2/1987 | Solazzi | 73/864.91 |
| 4,665,759 A | * | 5/1987 | Solazzi | 73/864.91 |
| 4,698,210 A | * | 10/1987 | Solazzi | 356/246 |
| 4,974,244 A | * | 11/1990 | Torrisi et al. | 378/45 |
| 5,253,280 A | * | 10/1993 | Mizuta | 378/45 |
| 5,451,375 A | * | 9/1995 | Solazzi | 422/549 |
| 5,454,020 A | | 9/1995 | Solazzi | |
| 5,630,989 A | * | 5/1997 | Solazzi | 422/557 |
| 5,703,927 A | | 12/1997 | Torrisi et al. | |

(Continued)

FOREIGN PATENT DOCUMENTS

| | | |
|---|---|---|
| EP | 2 158 967 A1 | 3/2010 |
| GB | 2 194 636 A | 3/1988 |

(Continued)

OTHER PUBLICATIONS

Toreki R., "The Glassware Gallery Powder X-Ray Diffractometers", Oct. 22, 2010.

*Primary Examiner* — Allen C. Ho
(74) *Attorney, Agent, or Firm* — Leason Ellis LLP

(57) ABSTRACT

A two or three part sample holder for X-ray apparatus has a sample ring 2 and a counter ring 20. The sample ring 2 has two opposed surfaces and foils 8, 10 one on each surface holding a powder sample 6 within the central hole 4. The sample ring 2 is relatively thin, of thickness 0.2 to 4 mm. A counter ring 20 is provided to engage with the sample ring 2 to provide increased strength and/or stiffness.

3 Claims, 3 Drawing Sheets

(56) References Cited

U.S. PATENT DOCUMENTS

| | | | | |
|---|---|---|---|---|
| 5,740,223 A * | 4/1998 | Ozawa | ............... | G01N 23/223 378/161 |
| 6,009,766 A * | 1/2000 | Solazzi | ............... | 73/864.91 |
| 6,428,751 B1 * | 8/2002 | Solazzi | ............... | 422/557 |
| 6,590,955 B2 * | 7/2003 | Matoba et al. | ............... | 378/44 |
| 6,603,544 B1 * | 8/2003 | Eckert | ............... | 356/246 |
| 7,535,989 B2 * | 5/2009 | Russell et al. | ............... | 378/44 |
| 7,722,821 B2 * | 5/2010 | Solazzi | ............... | 422/547 |
| 7,729,471 B2 * | 6/2010 | Burdett et al. | ............... | 378/47 |
| 7,981,380 B2 * | 7/2011 | Solazzi | ............... | 422/400 |
| 8,043,862 B2 * | 10/2011 | Solazzi | ............... | 436/172 |
| 8,404,197 B2 * | 3/2013 | Solazzi | ............... | 422/557 |
| 8,550,710 B2 * | 10/2013 | Kishida et al. | ............... | 378/208 |
| 2015/0016593 A1 * | 1/2015 | Larson et al. | ............... | 378/161 |

FOREIGN PATENT DOCUMENTS

| | | |
|---|---|---|
| JP | 10-038772 | 2/1998 |
| JP | 2005-345442 | 2/2005 |

\* cited by examiner

SAMPLE HOLDER

FIELD OF INVENTION

The invention relates to a sample holder, for use in X-ray measurement apparatus, and X-ray measurement using a sample holder.

BACKGROUND ART

In order to measure powder samples in X-ray fluorescence (XRF) apparatus, it is necessary that the sample be mounted in a sample holder which can in turn be placed in the apparatus.

However, conventional sample holders for powder usually have a significant contribution to the observed background intensity under the fluorescence peaks of interest caused by scattering in the sample holder wall material.

A number of different containers have been proposed for use in such X-ray fluorescence apparatus. In particular, examples are proposed in GB 2 194 636 and U.S. Pat. No. 4,037,109.

However, there remains a need for an improved method of X-ray fluorescence in which the effects of sample holders are minimised.

Further, there is a need for providing a sample holder that gives good results for X-ray fluorescence with a minimal volume of sample.

By way of example, during pharmaceutical research the amount of pharmaceutical prepared can often be very low and powder samples of only 0.1 g may need to be measured. The inventors tried using an existing sample cup for this powder but with such small quantities of sample the usable

SUMMARY OF INVENTION

Embodiments of the invention provide a sample holder and a method of carrying out X-ray fluorescence using the sample holder, the sample holder having a counter ring and a sample ring, in which a powder sample is held between a pair of films in a through hole in the sample ring.

The inventors have discovered that the sample holder according to the invention can provide good XRF results even with very small quantities of sample. In results presented below XRF results are achieved with a 0.1 g sample that are as good as when using 5 g sample in a conventional holder.

Such results are not achievable with conventional sample holders, such as conventional microcell holders.

The inventors have realised that even when X-rays are directed through the sample, and not directly irradiating the sidewalls of the sample holder, the powder in the sample holder can scatter the X-rays towards the side walls of the sample holder where the X-rays can interact with the sample holder and produce fluorescence or additional scattering. By reducing the thickness of the sample holder significantly, scattering and/or fluorescence from the walls of the holder, is reduced not just absolutely, but also as a fraction of the total measured scattered or fluorescence signal. The inventors have further realised that reducing the thickness of a sample holder reduces the stiffness of the sample holder.

This is particularly a problem when the sample is being held in place by very thin sheets, since the sample holder can become extremely flexible.

Accordingly, the sample holder may be a two-part or three-part sample holder with the inner sample ring fitting into a counter ring.

In this way, a maximum area of powder sample of minimum thickness can be measured. The reduction in sample thickness makes the sample transparent to high-energy X-rays which significantly reduces the background due to scattering. The sample holder shapes low mass loose powders for good measurements.

This in turn allows for improved lower limits of detection when making XRF measurements.

The sample holder thickness reduction allows small amounts of material to be handled and measured in the sample holder while remaining sufficiently stiff for keeping the sample flat and correctly located in the X-ray fluorescence apparatus. The counter ring provides additional stiffness than that provided by the sample ring alone. The sample holder is particularly relevant for determination of trace elements in relative high scattering matrix.

The counter ring may form a press fit with the sample ring. Alternatively, the counter ring may form a snap fit with the sample ring. In this way, the counter ring and sample ring may conveniently be brought together to form an integral unit without tools.

The films may be foils of thin polymer having a thickness from 1 to 50 μm.

Preferably, the materials used have low atomic number, not higher than 26.

The sample ring may be of polymer.

The counter ring may be of aluminium.

In the three-part arrangement, the sample holder further includes an outer ring arranged to engage the counter ring to form a unit of outer ring, counter ring and sample ring, the outer ring having a through hole arranged to align with the through holes of the counter and sample rings to pass X-rays.

One of the opposed films is held between the sample ring and the counter ring and the other of the opposed films is held between the counter ring and the outer ring. In this way, both films may be held between the rings.

The rings may be fitted together to hold the films without the use of adhesive.

In particular, the outer ring may form a press fit or a snap fit with the counter ring.

BRIEF DESCRIPTION OF DRAWINGS

For a better understanding of the invention, an embodiment will now be described, purely by way of example, with reference to the accompanying drawings, in which.

DETAILED DESCRIPTION OF CERTAIN EMBODIMENTS OF THE INVENTION

Figure 1:
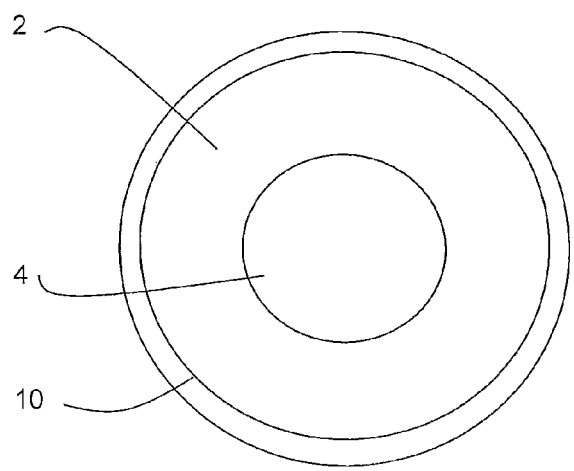
FIG. 1 shows a first half of the sample holder according to the embodiment.
Figure 2:
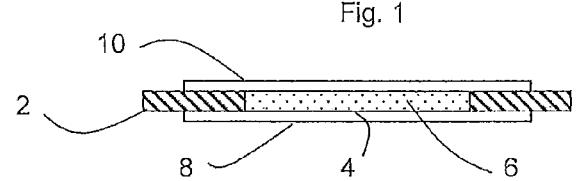
FIG. 2 shows a second half of the sample holder according to the embodiment.
Figure 3:
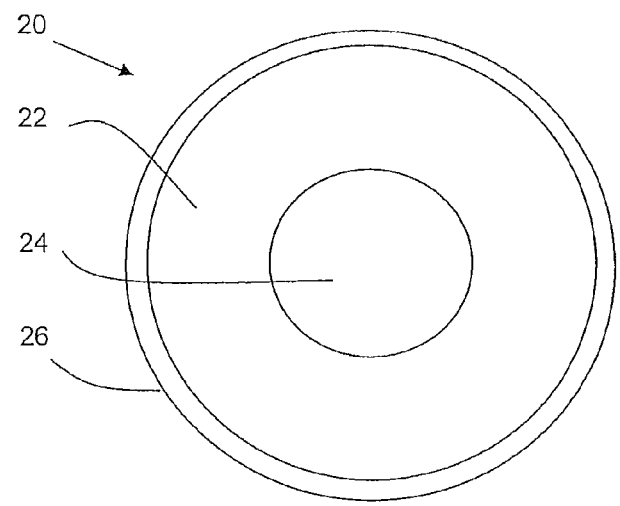
FIG. 3 shows a top view of counter ring for mounting the sample holder of the first embodiment.
Figure 4:
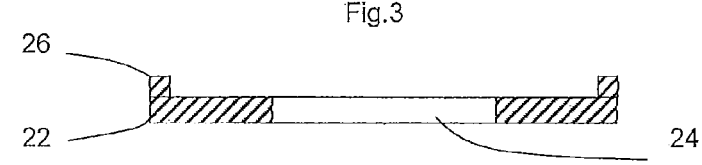
FIG. 4 shows a section through the counter ring of FIG. 3.

Referring to FIG. 1, a sample holder in the form of a sample ring, in the embodiment a circular sample disc 2 has a central hole 4 acting as a sample space for holding sample powder 6.

To retain the sample powder 6, opposed foils 8, 10 are provided, one on each opposed face of the circular sample disc 2.

The foils 8 and 10 are thin—for example 1 μm to 50 μm, especially 3 to 20 μm. In the specific embodiment shown, the foils 8 and 10 are 4 μm to 6 μm thick. The circular sample disc 2 is typically 0.5 mm to 2 mm, preferably 0.75 mm to 1.5 mm thick. The diameter of the central hole 4 may be in the range 5 mm to 50 mm, preferably 10 mm to 20 mm, and the central hole 4 typically holds 10 to 200 mg of powder.

The foil 8 and 10 is of polymer, for example NYLON or MYLAR. Likewise, the circular sample disc 2 is of polymer, and may conveniently be of the same material. Low atomic number materials are preferred, to avoid fluorescence.

The foil 8 and 10 does not cover the whole of the opposed surfaces of the circular sample disc 2.

In view of the materials choice and thickness of the circular sample disc 2, the circular sample disc 2 and the foils 8 and 10 are flexible which can give rise to handling difficulties, especially in manufacturing environments.

Accordingly, a counter ring 20 is provided that fits together with the circular sample disc 2 to provide additional support. The counter ring 20 is in the form of a ring 22 with a central through hole 24 arranged to correspond with the central hole 4 of the circular sample disc 2 to allow X-rays to pass.

The counter ring 20 has a raised outer ring 26 in which the radially inner face is arranged to engage the outer circumference of the circular sample disc 2.

In the embodiment shown, the counter ring 20 engages with the circular sample disc 2 by a press fit. However, in alternative embodiments detent means may be provided to allow a snap fit.

The complete sample holder with counter ring 20 engaged with circular sample disc 2 is sufficiently robust and in particular rigid to be able to be used in industrial environments. The counter ring 20 provides some measure of protection to foil 10 to allow the sample holder to be placed on a surface with the counter ring 20 against the surface without damage.

In some cases, such sample holders may be used in existing equipment replacing existing sample holders with the same form factor but providing improved performance.

The counter ring 20 may be made of plastics, for example the same plastics as the sample ring.

Alternatively, the counter ring 20 may be made, in all or in part, of metal. Preferably, a metal of atomic number no higher than 26 is used. The counter ring 20 may in particular be made of aluminium.

The circular sample disc 2 need not be in the form of a circular disc, but instead may be for example square or rectangular. Likewise, the through holes may be square, circular or rounded as appropriate for individual X-ray fluorescence apparatus.

Results using 0.1 g of pharmaceutical powder in a prototype sample holder were measured and compared with those using a 5 g self standing pellet of the same material and with 5 g of powder in a conventional "P1" cup.

To compare samples, the root mean square deviation (RMS) in parts per million were obtained using XRF for three elements, Ru, Pd and Pt, for the three samples.

| | Element | | |
|---|---|---|---|
| | RMS Ru | RMS Pd | RMS Pt |
| 5 g, pellet self standing | 0.29 | 0.18 | 0.33 |
| 5 g, powder in P1 cup | 0.51 | 0.20 | 0.17 |
| 0.1 g powder in holder | 0.19 | 0.16 | 0.20 |

These results demonstrate that similar levels of deviation may be obtained using very small quantities of sample.

Figure 5:
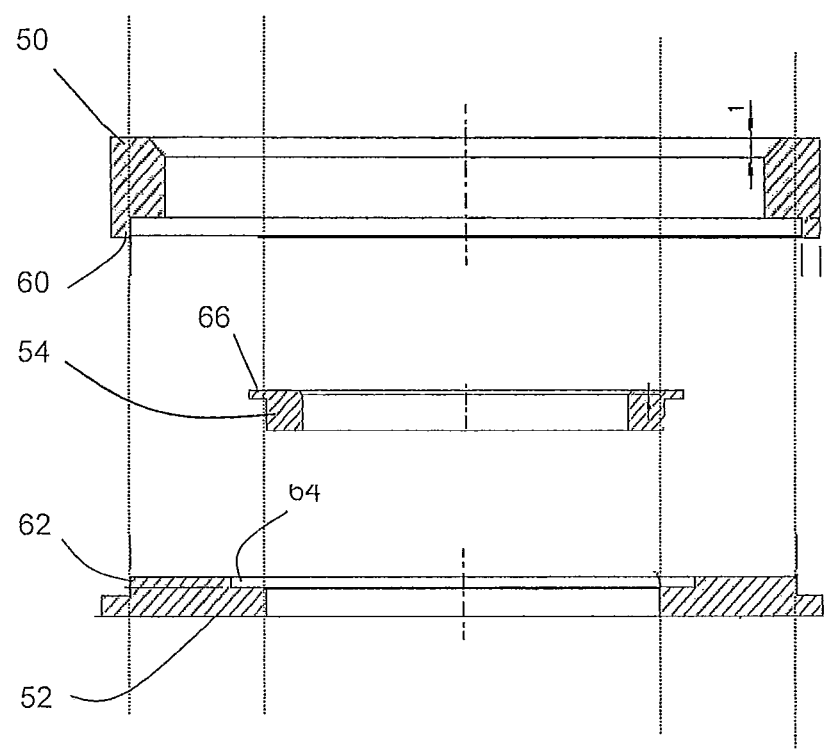
FIG. 5 shows sections through three parts of a sample holder according to a second embodiment.
Figure 6:
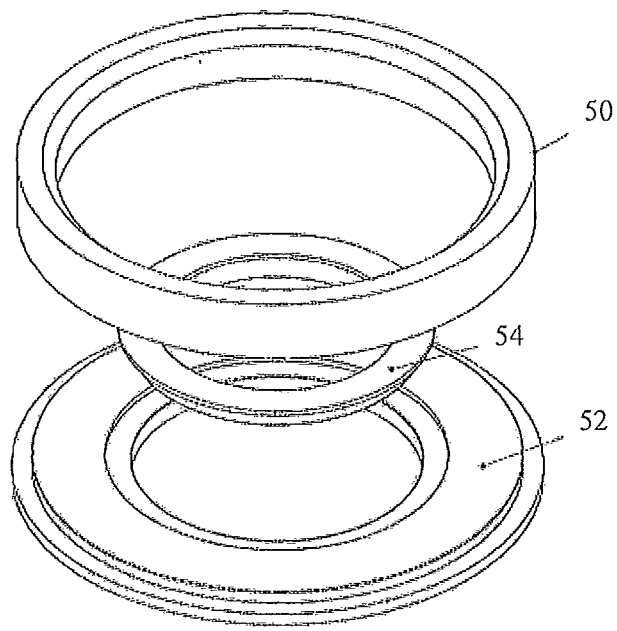
FIG. 6 shows a perspective view of the three parts separately.
Figure 7:
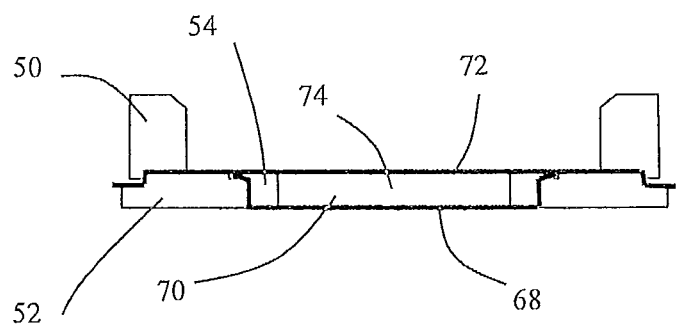
FIG. 7 shows the three parts mounted together with a sample powder.

An alternative arrangement is shown in FIGS. 5 to 7. In this case, there are three rings 50, 52, and 54, an outer ring 50, a counter ring 52 and a sample ring 54, shown in section in FIG. 5. Dotted construction lines indicate aligned parts.

The three rings are arranged to fit together with the outer ring 50 having an outer retaining ring 60 on its lower side adapted to mate with an outer step 62 on the upper edge of the counter ring 52. The counter ring 52 has an inner step 64 arranged to mate with an outer flange 66 on the sample ring 54.

In use a first foil 68 is stretched across the lower surface of sample ring 54 and then the sample ring 54 is mounted into counter ring 52 which retains the first foil 68 stretched along the bottom surface of sample ring 54. A powder sample 74 is then mounted above the first foil 68 in central cavity 70.

A second foil 72 is then mounted on the upper surface of the counter ring 52 and sample ring 54 extending to the outer edge of the counter ring 52. The counter ring 52 is then mounted to the underside of outer ring 50 stretching the second foil 72. Thus, the powder sample 74 is held between the first and second foils 68, 72. Note that in FIG. 7 the foils 68 and 72 are shown with thick lines for clarity but in fact the foils 68 and 72 are relatively thin.

In this way the powder sample 74 can be held in place without the need for glue. In particular, in this embodiment the rings 50, 52, and 54 are held together by a press fit. Alternatively, a snap fit may be used.

Alternatively, for greater security, glue or other adhesive can be used to fix the rings 50, 52, and 54 together.

In this arrangement all the rings 50, 52, and 54 can be made of the same or of a combination of different materials such as polymer and/or aluminium.

The sample holder of embodiments of the invention can minimise the exposure of holder material to the excitation X-ray beam. This reduces the amount of holder material that can scatter and so the spectral background component can be reduced.

The sample holder of embodiments of the invention does not need to be absolutely leakproof unless the sample is toxic or biologically active.

The sample holder of embodiments of the invention does not require screws and so is easy, simple and safe to use. The sample holder can avoid contamination of the sample by humidity.

Thus, while there have been shown, described, and pointed out fundamental novel features of the invention as applied to several embodiments, it will be understood that various omissions, substitutions, and changes in the form and details of the illustrated embodiments, and in their operation, may be made by those skilled in the art without departing from the invention. Substitutions of elements from one embodiment to another are also fully intended and contemplated. The invention is defined solely with regard to the claims appended hereto, and equivalents of the recitations therein.

What is claimed is:

1. A method of carrying out X-ray fluorescence measurements on a powder sample, comprising:

placing the powder sample within a central through hole of a sample ring (2,54) having opposed surfaces, the sample ring having a thickness of 0.2 mm to 4 mm between the opposed surfaces, the central through hole having a maximum lateral dimension of 5 mm to 50 mm;

providing opposed films (8,10,68,72) of thickness 1 to 50 µm on the opposed surfaces sealing the central through hole to retain the powder sample in the central through hole;

engaging a counter ring (20,52) with the sample ring to form a first unit, the counter ring having a central through hole arranged to align with the central through hole in the sample ring;

mounting an outer ring (50) to engage the counter ring (52) to form a second unit of the outer ring, the counter ring, and the sample ring, the outer ring (50) having a through hole arranged to align with the central through holes hole of the counter ring and the central through hole of the sample ring; and mounting the second unit in an X-ray fluorescence apparatus and passing X-rays through the central through hole of the counter ring to the powder sample to carry out X-ray fluorescence measurements.

2. A method of carrying out X-ray fluorescence measurements on a powder sample, comprising:

stretching a first foil across a lower surface of a sample ring having a central through hole;

mounting a counter ring around the sample ring to retain the first foil stretched across the lower surface of the sample ring;

filling powder sample into the central through hole above the first foil;

mounting a second foil on the an upper surface of the counter ring and the sample ring; and mounting an outer ring outside the counter ring to maintain the second foil stretched and the powder sample held between the first foil and the second foils foil in the central through hole of the sample ring.

3. The method according to claim 2, wherein the first foil and the second foil are of thin polymer having a thickness of from 3 to 20 µm.

* * * * *